US00PP14370P29

(12) United States Plant Patent
Turrell et al.

(10) Patent No.: US PP14,370 P2
(45) Date of Patent: Dec. 16, 2003

(54) BUDDLEIA PLANT NAMED 'MONRELL'

(50) Latin Name: *Buddleia davidii*
Varietal Denomination: Monrell

(75) Inventors: Susan Turrell, Carlton, OR (US); Philip Turrell, Carlton, OR (US)

(73) Assignee: Monrovia Nursery Company, Azusa, CA (US)

( * ) Notice: Subject to any disclaimer, the term of this patent is extended or adjusted under 35 U.S.C. 154(b) by 0 days.

(21) Appl. No.: 10/259,938

(22) Filed: Sep. 29, 2002

(51) Int. Cl.[7] ..... A01H 5/00
(52) U.S. Cl. ..... Plt./242
(58) Field of Search ..... Plt./242

*Primary Examiner*—Bruce R. Campell
*Assistant Examiner*—June Hwu
(74) *Attorney, Agent, or Firm*—C. A. Whealy

(57) ABSTRACT

A new and distinct Buddleia plant named 'Monrell', characterized by its upright and outwardly spreading plant habit; green and pale yellow variegated foliage; freely branching and freely flowering habit; and light purple-colored flowers arranged on cone-shaped panicles.

1 Drawing Sheet

Botanical classification/cultivar designation: *Buddleia davidii* cultivar Monrell.

BACKGROUND OF THE INVENTION

The present invention relates to a new and distinct cultivar of Buddleia, botanically known as *Buddleia davidii*, and hereinafter referred to by the name 'Monrell'.

The new Buddleia is a naturally-occurring branch mutation of the *Buddleia davidii* 'Pink Delight', not patented. The new Buddleia was discovered and selected by the Inventors in a controlled environment in Carlton, Oreg. in June, 1997.

Asexual reproduction of the new Buddleia by cuttings taken in a controlled environment in Carlton, Oreg., since June, 1997, has shown that the unique features of this new Buddleia are stable and reproduced true to type in successive generations.

SUMMARY OF THE INVENTION

The cultivar Monrell has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Monrell'. These characteristics in combination distinguish 'Monrell' as a new and distinct cultivar:

1. Upright and outwardly spreading plant habit.
2. Green and pale yellow variegated foliage.
3. Freely branching and freely flowering habit.
4. Light purple-colored flowers arranged on cone-shaped panicles.

Compared to plants of the parent, the cultivar Pink Delight, plants of the new Buddleia are more compact. In addition, plants of the new Buddleia have variegated leaves whereas plants of the cultivar Pink Delight have solid green-colored leaves.

Plants of the new Buddleia can be compared to plants of the Buddleia cultivar Harlequin, not patented. In side-by-side comparisons conducted in Carlton, Oreg., plants of the new Buddleia differed from plants of the cultivar Harlequin in the following characteristics:

1. Plants of the new Buddleia had green and pale yellow variegated foliage whereas plants of the cultivar Harlequin had green and white variegated foliage.
2. Plants of the new Buddleia had lighter purple-colored flowers than plants of the cultivar Harlequin.

BRIEF DESCRIPTION OF THE PHOTOGRAPHS

The accompanying colored photographs illustrate the overall appearance of the new Buddleia, showing the colors as true as it is reasonably possible to obtain in colored reproductions of this type. Colors in the photographs may differ slightly from the color values cited in the detailed botanical description which accurately describe the colors of the new Buddleia.

The photograph at the top of the sheet comprises a side perspective view of a typical flowering plant of 'Monrell' grown in a container.

The photograph at the bottom left of the sheet is a close-up view of typical inflorescences and leaves of 'Monrell'.

The photograph at the bottom right of the sheet is a close-up of typical flowers of 'Monrell'.

DETAILED BOTANICAL DESCRIPTION

The aforementioned photographs and following observations and measurements describe plants grown in Azusa, Calif., grown in one-gallon containers in an outdoor nursery during the spring and early summer and under conditions which closely approximate commercial production. During the production of the plants, day temperatures averaged 18° C. and night temperatures averaged 10° C. Plants were about nine months old when the photographs and the description were taken. In the description, color references are made to The Royal Horticultural Society Colour Chart, 1995 Edition, except where general terms of ordinary dictionary significance are used.

Botanical classification: *Buddleia davidii* cultivar Monrell.

Parentage: Naturally-occurring branch mutation of *Buddleia davidii* cultivar Pink Delight, not patented.

Propagation:

*Type.*—By cuttings.

*Time to initiate roots.*—About 15 days at a temperature of 21° C.

*Time to produce a rooted young plant.*—About 90 days at a temperature of 21° C.

*Root description.*—Fine; whitish in color.

*Rooting habit.*—Moderately dense; freely branching.

Plant description:

*Plant form and growth habit.*—Upright and outwardly spreading plant habit; open and loose plant form; relatively compact, appropriate for container production; perennial shrub. Low to moderately vigorous growth habit.

*Branching habit.*—Freely branching, usually about six to eight lateral branches develop after plants are pinched.

*Plant height.*—About 75 cm.

*Plant diameter* (*area of spread*).—About 120 cm.

*Lateral branch description.*—Length: About 25 to 60 cm. Diameter: About 4 mm. Internode length: About 3.5 to 4 cm. Texture: Pubescent. Color: Young stems: 195A. Woody stems: 199A to 199B.

*Foliage description.*—Arrangement: Opposite, simple. Orientation: Reflexed. Length: About 9.75 cm. Width: About 2.75 cm. Shape: Elliptic. Apex: Acuminate. Base: Attenuate. Margin: Irregular and finely serrate. Texture, upper and lower surfaces: Pubescent; rugose. Venation pattern: Pinnate, arcuate. Color: Young leaves, upper surface: Center, 147B; surrounded by 146C extending to the margin. Young leaves, lower surface: Center, 194A; surrounded by more gray than 145C extending to the margin. Fully expanded leaves, upper surface: Center, 147B, with random splotches of 148C; surrounded by 4D extending to the margin. Fully expanded leaves, lower surface: Center, 194B; surrounded by 4D extending to the margin. Venation, upper and lower surfaces: Same as lamina. Petiole: Length: About 5 mm. Diameter: About 1.5 mm. Texture, upper and lower surfaces: Smooth, glabrous. Color, upper and lower surfaces: 194B to 194C.

Flower description:

*Flower arrangement/appearance.*—Small salverform four-lobed flowers arranged on terminal and axillary panicles; panicles cone-shaped. Freely flowering with usually about 1,200 flowers per panicle. Panicles initially upright, then curving somewhat downward; flowers face upright or outward. Flowers persistent; individual flowers last about two to three days on the plant.

*Natural flowering season.*—Late spring and summer.

*Fragrance.*—Faint; sweet, light floral.

*Panicle length.*—About 10 to 15 cm.

*Panicle diameter.*—Towards the base: About 5.5 to 6 cm. Towards the apex: About 3 cm.

*Flower diameter.*—About 7 mm.

*Flower* (*tube*) *length.*—About 1 cm.

*Flower tube diameter, at base.*—About 1 mm.

*Flower buds.*—Length: About 8 mm. Diameter: About 1 mm. Shape: Oblong, elongate. Color: 82A to 82B.

*Petals.*—Arrangement: Four or occasionally five petals fused into a tubular corolla with petal lobes flaring abruptly. Lobe length: About 3 mm. Lobe width: About 2 mm. Shape: Rounded. Apex: Rounded. Base: Fused. Margin: Entire. Texture, upper and lower surfaces: Smooth, glabrous. Color: When opening, upper surface: 77B. When opening, lower surface: 77C. Fully opened, upper surface: 77C to 77D; with development, color becoming closer to 75A to 75B and towards the base, 76D. Fully opened, lower surface: 77D. Throat: 23A. Tube: 70B to 70C. Throat: 53A.

*Sepals.*—Appearance: Four sepals fused into a tubular calyx. Length: About 3 mm. Width: About 1.5 mm. Shape: Narrowly oblong. Apex: Acute. Base: Fused. Margin: Entire. Texture, upper and lower surfaces: Smooth, glabrous. Color, upper and lower surfaces: 194B.

*Peduncles.*—Length: About 1.5 to 2 cm. Diameter: About 2.5 mm. Strength: Strong. Texture: Smooth, glabrous. Color: 194A.

*Pedicels.*—Length: About 2 mm. Diameter: About 1 mm. Strength: Strong. Texture: Smooth, glabrous. Color: 194A.

*Reproductive organs.*—Androecium: Stamen number: About four per flower. Anther shape: Oblong. Anther length: Less than 1 mm. Anther color: 162C. Amount of pollen: Scarce. Pollen color: 162C. Gynoecium: Pistil number: One per flower. Pistil length: About 3 mm. Style length: About 2 mm. Style color: 145C. Stigma shape: Oblong, elongate. Stigma color: 145A. Ovary color: 145A.

*Fruit/seed.*—Fruit and seed production has not been observed.

Disease/pest resistance: Plants of the new Buddleia have not been observed to be resistant to pathogens and pests common to Buddleia.

Hardiness: Plants of the new Buddleia are hardy to USDA zone 7.

It is claimed:

1. A new and distinct Buddleia plant named 'Monrell', as illustrated and described.

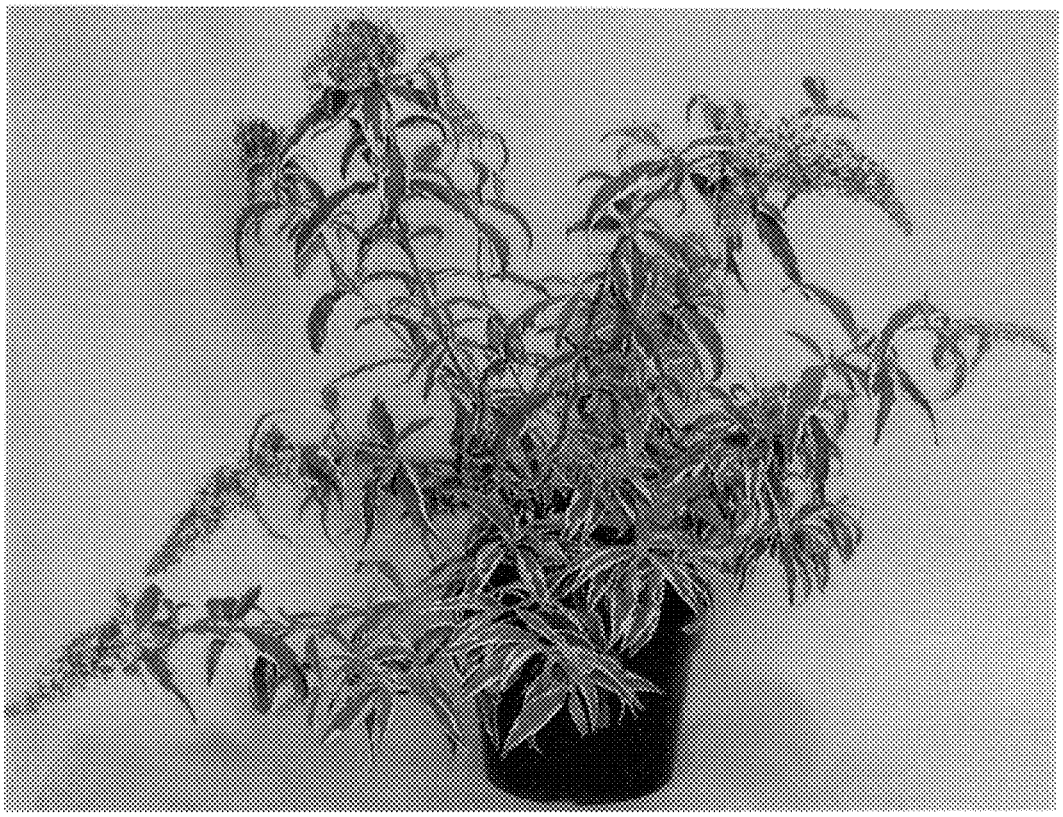
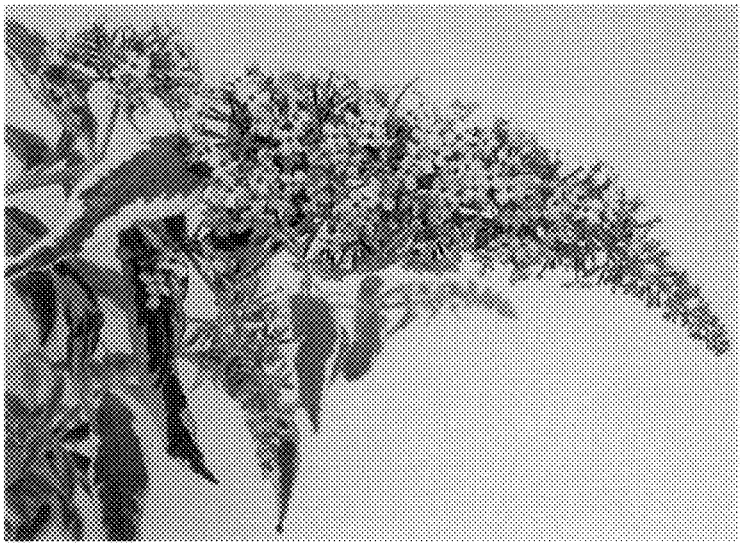
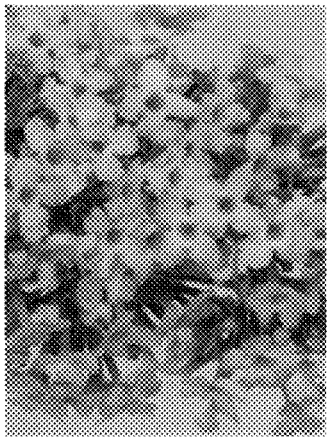

* * * * *